(12) United States Patent
Magneson et al.

(10) Patent No.: US 8,562,343 B2
(45) Date of Patent: Oct. 22, 2013

(54) FLUID DRIVEN DENTAL HANDPIECE WITH HYDROSTATIC BEARINGS

(75) Inventors: Allan Magneson, Sherwood Park (CA); Michael D. Neary, Bryn Mawr, PA (US); Victor K. Obeid, Collegeville, PA (US)

(73) Assignee: Allan Magneson, Sherwood Park, Alberta (CA)

(*) Notice: Subject to any disclaimer, the term of this patent is extended or adjusted under 35 U.S.C. 154(b) by 164 days.

(21) Appl. No.: 13/134,410

(22) Filed: Jun. 7, 2011

(65) Prior Publication Data

US 2011/0306011 A1 Dec. 15, 2011

Related U.S. Application Data

(60) Provisional application No. 61/397,531, filed on Jun. 11, 2010.

(51) Int. Cl.
*A61C 1/05* (2006.01)

(52) U.S. Cl.
USPC .......................................... 433/132

(58) Field of Classification Search
USPC ............ 433/114–133; 409/904; 415/111, 904
See application file for complete search history.

(56) References Cited

U.S. PATENT DOCUMENTS

| | | | |
|---|---|---|---|
| 3,088,707 A * | 5/1963 | Williams et al. | 415/112 |
| 3,128,988 A * | 4/1964 | Mandroian | 415/202 |
| 3,147,551 A * | 9/1964 | Seegers | 433/132 |
| 3,210,044 A * | 10/1965 | Mori | 415/101 |
| 3,380,162 A * | 4/1968 | Heathe | 433/132 |
| 3,384,344 A * | 5/1968 | Ota | 415/51 |
| 3,391,902 A | 7/1968 | Dee | |
| 3,408,043 A * | 10/1968 | Williams et al. | 415/113 |
| 3,411,212 A * | 11/1968 | Staunt | 433/87 |
| 3,471,125 A * | 10/1969 | Otto et al. | 415/112 |
| 3,955,284 A | 5/1976 | Balson | 32/27 |
| 4,153,993 A | 5/1979 | Kataoka et al. | 32/27 |
| 4,209,293 A * | 6/1980 | Sugai et al. | 433/132 |
| 5,340,312 A * | 8/1994 | Murase | 433/132 |
| 5,562,446 A * | 10/1996 | Matsui et al. | 433/132 |
| 6,994,475 B2 * | 2/2006 | Doll et al. | 384/492 |
| 7,677,890 B2 | 3/2010 | Turner | 433/127 |
| 2008/0070189 A1* | 3/2008 | Turner | 433/132 |
| 2008/0090202 A1* | 4/2008 | Browning et al. | 433/104 |

FOREIGN PATENT DOCUMENTS

| | | |
|---|---|---|
| JP | 09-047460 | 2/1997 |
| WO | WO/2003/020152 | 3/2003 |
| WO | WO 03-071973 | 9/2003 |

* cited by examiner

*Primary Examiner* — Robyn Doan
*Assistant Examiner* — Matthew Nelson
(74) *Attorney, Agent, or Firm* — Michael F. Petock, Esq.; Petock & Petock, LLC

(57) ABSTRACT

A dental handpiece uses a single airflow input to drive both a rotor and provide a hydrostatic bearing. The fluid flow in the form of compressed air is applied first to the hydrostatic bearings and then subsequently to the turbine blades of the rotor without the use of any moving mechanical parts by the design of the air passageway being more direct for the hydrostatic bearing. This passageway is the form of a manifold insert which may be mounted within the handpiece. The handpiece includes a pair of frusto-conical cages separated by a C-shaped spacer which enables precise fabrication. The frusto-conical ends of the rotor and the mating frusto-conical inner surfaces of the cages are provided with a diamond like carbon coating.

15 Claims, 10 Drawing Sheets

FLUID DRIVEN DENTAL HANDPIECE WITH HYDROSTATIC BEARINGS

CROSS REFERENCE TO RELATED APPLICATION

This application claims the benefit of the filing date of provisional application No. 61/397,531 entitled Fluid Driven Dental Handpiece With Hydrostatic Bearings filed Jun. 11, 2010 by the inventors herein.

FIELD OF THE INVENTION

The present invention relates to a fluid, such as compressed air, driven dental handpiece with hydrostatic bearings. More particularly, the present invention relates to a fluid driven dental handpiece with hydrostatic bearings wherein structure is provided to regulate the relative flow to the driving turbine and the hydrostatic bearing structure to provide fluid flow to the bearings prior to activating rotation of the rotor. The term "fluid" as used throughout includes air such as compressed air or any other fluid.

BACKGROUND OF THE INVENTION

Dental handpieces for use for drilling, burnishing and other dental operations are widely used today with high speed rotation of a tool held in a head of a dental handpiece by a chuck. Dental handpieces widely used today employ bearing systems that utilize expensive precision rolling element bearings that are subject to wear, cause damaging high frequency noise and require frequent lubrication. The ongoing wear process requires that the user frequently send handpieces out for repair or rebuilding. This requires the user to have a multiplicity of handpieces available to continue dental practice as faulty units are being repaired or rebuilt. The requirement for lubrication of rolling element bearings after any autoclave and/or cleaning process is counter to the requirement that the tooth preparation surface be impeccably clean and oil free in order for dental preparations to adhere to the tooth surface.

SUMMARY OF THE INVENTION

An advantage of the present invention is that it provides that a single fluid source may be utilized to drive a turbine which drives a spindle with a chuck for holding a dental bur or other tool and for supplying fluid such as compressed air to the hydrostatic bearings.

Another advantage of the present invention is that switching of the fluid or air flow for driving of the turbine and operation of the hydrostatic bearings may be controlled without moving parts.

Another advantage of the present invention is that the means for controlling the fluid flow for the drive turbine and the gas bearings may be in the form of a manifold.

Another advantage of the present invention is that the manifold may be provided in the form of a manifold insert which enables it to be incorporated into a small dental handpiece which is adapted to fit within the mouth of a dental patient.

Another advantage of the present invention is that it provides an economical hardware design to properly size a highly precise gas hydrostatic bearing for use in a dental handpiece.

Another advantage of the present invention is that it employs a manifold insert design which reduces the physical size of the dental handpiece grip while providing low flow restriction passageways for the hydrostatic bearings gas.

Another advantage of the present invention is that it utilizes a pneumatic valve in the manifold insert to energize the gas bearings first and to secondly energize the turbine for rotational motion.

Another advantage of the present invention in that the pneumatic valve in the manifold insert contains no moving parts.

Another advantage of the present invention is that it provides the surface of the hydrostatic bearing with a surface which improves the lubricity of the components at the times of start up and shut down.

Briefly and basically, the invention comprises a dental handpiece or similar structure having a relatively small diameter handle with a grip portion with a head or end piece attached to it, with a turbine driven spindle in the head which receives fluid through the handle both for driving the turbine of the spindle and for providing fluid for hydrostatic bearings. The grip of the handle includes a manifold, which is preferably a manifold insert, which provides a straight conduit or otherwise more direct passageway for supplying bearing fluid supply and an angled or less direct turbine drive passageway which enables switching of the fluid flow so that fluid flow such as compressed air is supplied to the hydrostatic bearings prior to it being applied to the turbine so that the bearings are activated before rotation of the spindle begins. The present invention further includes a coupling tube mounted in the path of the angled turbine drive passageway to adjust the relative fluid flow between the straight passageway to the bearing supply and the angled passageway to the turbine. The coupling tube may be adjusted by adjusting preferably its inner diameter.

A cartridge in the head utilizes two end cages of identical design with conical form for a hydrostatic gas bearing of frusto-conical shape to support the rotor in both the radial and axial directions simultaneously.

Machined stop shoulders on identical and interchangeable stator cages combined with a C shaped spacer provide a stable and self aligning platform to affix the cages and spacer together with welds to provide an air tight seal for the components.

The machined stop shoulders on the interchangeable cages are selected to be of a height in which they almost touch when using the shortest length sizing C-shaped spacer to minimize volume about the turbine cavity and maximize the effect of the moving turbine air to impart energy to the turbine which is frictionally attached to the rotor and bearing cones.

In order to enable the grip area of a dental handpiece to be slender for adequate ability to be grasped by the fingers and inserted into a confined space such as the mouth of a dental patient, a manifold insert is used to minimize the physical grip size by reducing the number of tubings and tubing connections within the slender grip component.

By use of a manifold insert which is incorporated to minimize the physical grip size while reducing air flow restrictions for the bearings by use of machined channels, the combined cross sectional area of the channels is formed to be larger than the supply tubing, in both the head and manifold insert mounting faces, so that the effect of the pressure drop to the gas bearings in torturous air passageways is minimized while the manifold insert also provides a straight, non-torturous path for the turbine drive gas.

The manifold insert includes a pneumatic valve in that a stream of air with a velocity passes over a second tube angled to a first tube thereby drawing slight vacuum on the second or angled tube until overall system back pressure builds, wherein the first or straight tube immediately provides readily available airflow and air pressure to the bearings before the second aforementioned tube provides air to the turbine. This arrangement serves to energize the hydrostatic gas bearings first and the turbine secondly, thereby providing non-contact bearing function prior to providing rotor revolution.

By use of an adjustable coupling tube of the present invention to attach the manifold insert to the drill head, it is possible to segregate turbine air from that of bearing air, and by selecting a properly sized coupling tube-wall thickness, the delivery of air between the turbine and the air bearing can be suitably balanced.

Further, the attachment of the manifold insert to the drill head by use of a selectably changeable coupling tube to segregate turbine air from that of bearing air, and by selecting a properly sized coupling tube wall thickness, power output performance of the turbine rotor assembly verses bearing load carrying capacity can be balanced.

The present invention further includes the use of a double ended rotor equipped with outwardly facing frusto-conical gas bearings to carry a combined radial and axial load, and this bearing surface may be coated with a conformal carbon coating such as diamond like coating DLC to reduce non-lubricated frictional coefficient properties of the rotor journals sliding against the fixed stator bearing components during potential periods of contact immediately upon commencing or at the cessation of rotor revolution.

The present invention further includes a vent hole in the system component opposite the cutting bur end which can be utilized to permit venting and balancing of the doubled ended rotor equipped with outwardly facing frusto-conical gas bearings so that the bearings of either end of the rotor are able to vent the working bearing gas in an equitable and favorable ratio from bearing to bearing for establishing stable high speed operation and bearing load carrying capacity.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

DETAILED DESCRIPTION OF THE PREFERRED EMBODIMENTS

Figure 1:
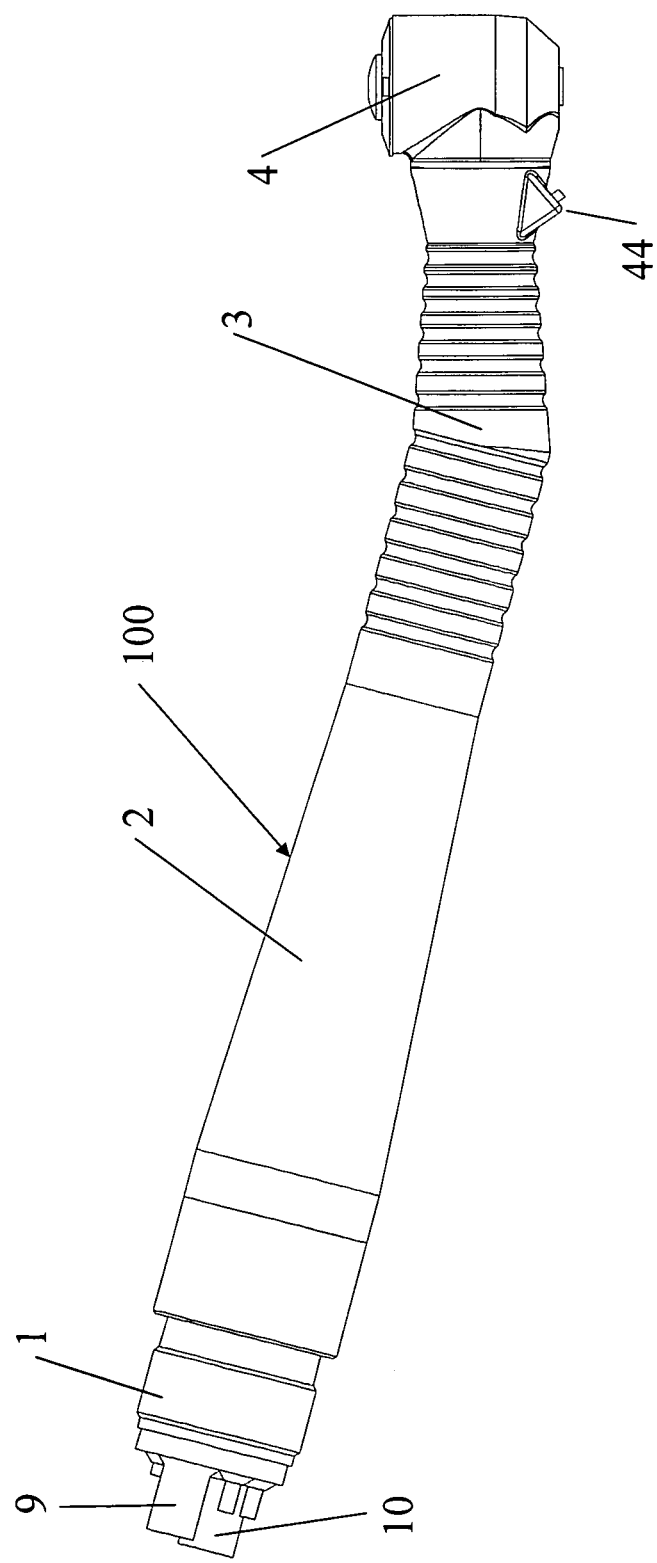
FIG. 1 is a side elevation view of a dental handpiece in which the relative sizes of the handle, grip and head are visible.

Referring now to the drawings, wherein like numerals indicate like elements, there is shown in FIG. 1 a dental handpiece 100 in accordance with the present invention. It is understood that the handpiece 100 may be utilized in other applications other than dentistry where a small handpiece is required to provide fluid input and exhaust for a high speed drill. Handpiece 100 includes a connector 1 which may be an ISO 9168-type B connector. Other suitable connectors may be utilized. Handpiece 100 further includes a generally cylindrical handle 2 and a slender elliptically shaped grip 3 and a head 4 which contains a hydrostatic gas bearing cartridge which includes a turbine driven rotor with a chuck for holding a tool as well as the hydrostatic bearings. Also shown in FIG. 1 is the fluid input or compressed air supply tube 9 and exhaust tube 10. Also shown in FIG. 1 is a triangular projection 44 formed on grip 3 which has one or more lights, preferably two spaced lights in the form of fiber optic endings and a compressed air and water spray output, preferably in the form of a water spray concentrically mounted within an air spray for aid in removal of drilling debris.

Figure 2:
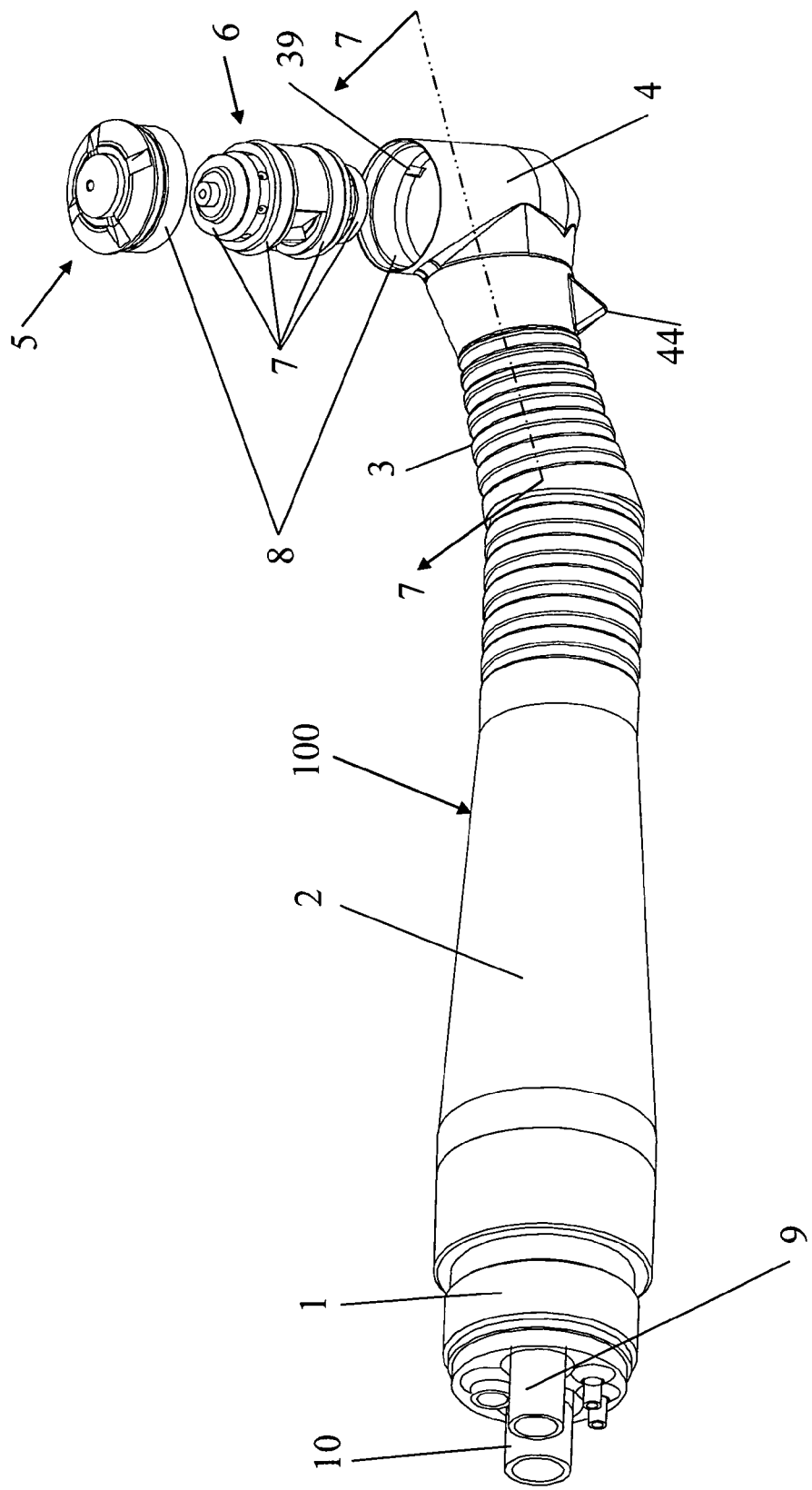
FIG. 2 is a view in perspective of the dental handpiece of FIG. 1, with a partially exploded head illustrating, inter alia, a securing cap with a vent hole and a hydrostatic gas bearing cartridge assembly.

Referring now more particularly to FIG. 2, there is shown an exploded view of the interior structure of head 4 which includes a cap assembly 5 and a fluid hydrostatic bearing cartridge 6. Bearing cartridge assembly 6 is mounted on elastomeric seal 7 of low shore durometer for sealing and as a means of providing dampening against rotor instabilities. Cap assembly 5 is removably fixed to the handpiece head 4 by means of mating machine screw threads 8 on cap 5 and inner surface of head 4. The purpose of the cap 5 is to create an axial sealing means for the cartridge 6 by means of the elastomeric seals 7. The fluid input tube 9 provides the input tube for the drive fluid, which is preferably compressed air, for both the hydrostatic bearings and the turbine driven rotor. The larger diameter exhaust tube 10 is the exhaust for both the bearings and the turbine drive. Also visible within head 4 is a broached slot 39 which receives an anti-rotation pin 12, best seen in FIG. 3, which prevents rotation of gas hydrostatic bearing cartridge 6.

Figure 3:
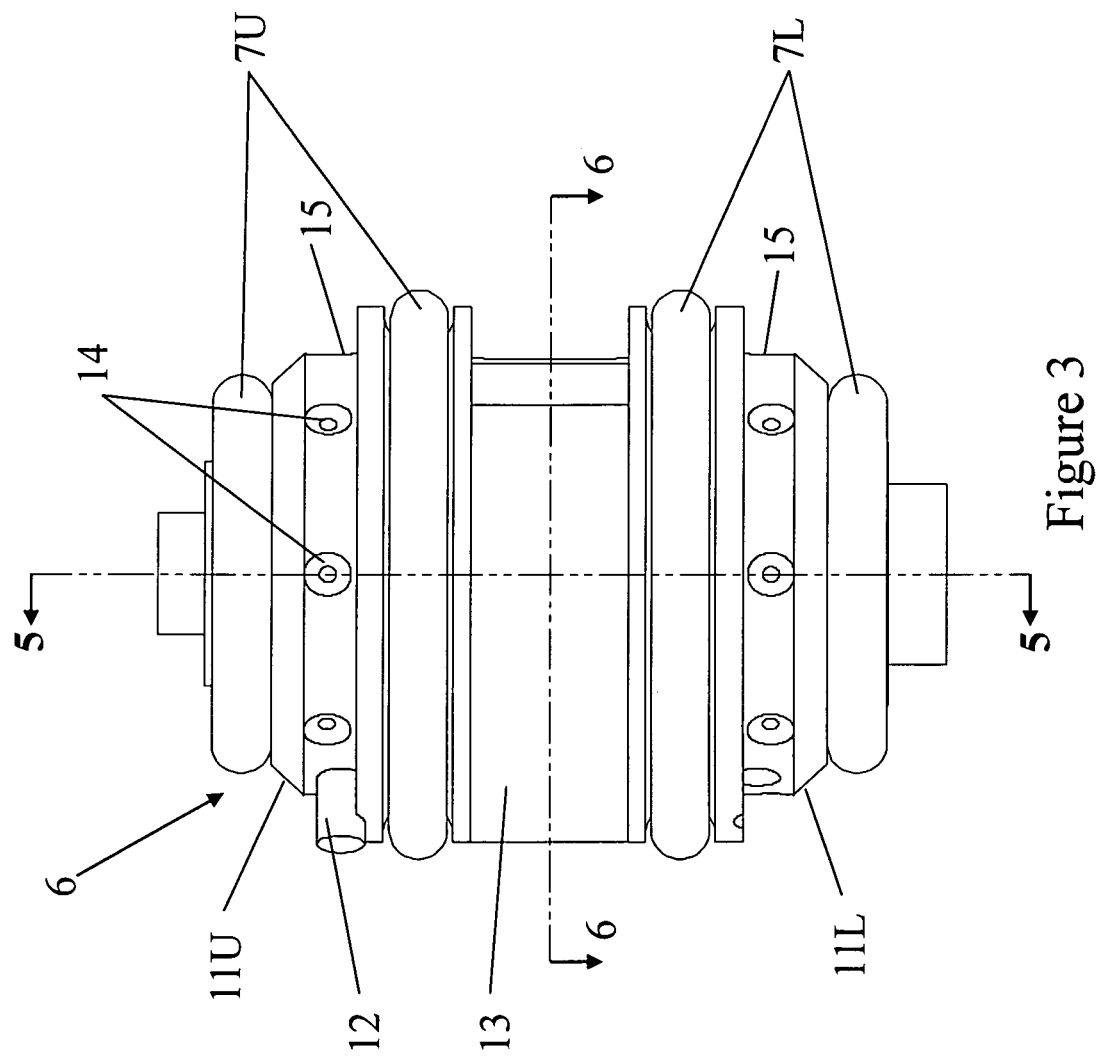
FIG. 3 is an elevation view of the hydrostatic gas bearing cartridge assembly.

Referring now more particularly to FIG. 3, there is shown the hydrostatic bearing cartridge assembly 6 which is comprised of identical and interchangeable upper static bearing component 11U and an interchangeable lower static bearing component 11L, which may be referred to as cages. C shaped spacer 13 separates interchangeable upper static bearing component 11U and interchangeable lower static bearing component 11L. Bearing clearances are set by a selected properly sized C shaped spacer 13. Four elastomeric seals 7U and 7L cushion and seal the bearing fluid or air supply plenums. The plenums are formed between the upper seal 7U, the exterior portion of interchangeable upper static bearing component 11U and the inner surface of head 4. In a similar manner, the lower plenum is formed between elastomeric seals 7L, the outer surface of interchangeable lower static bearing component and the inner surface of head 4. Dowel or pin 12 prevents rotation of hydrostatic bearing cartridge 6. Pin 12 may be engaged in recess 38 and in the inner surface of head 4 as seen in FIG. 2. An opening is provided for a pin in interchangeable lower static bearing component 11L, but only one pin is necessary to prevent rotation of hydrostatic bearing cartridge 6. The upper and lower hydrostatic bearings are supplied with working fluid, such as compressed air, via a multiplicity of countersunk orifices 14, all of which are, on a single upper or lower cage, connected via a circumferential groove 15 for forming a part of the aforesaid plenum to permit the flow of an ample supply of compressed air or other gas to all sectors of the hydrostatic gas bearing.

Figure 4:
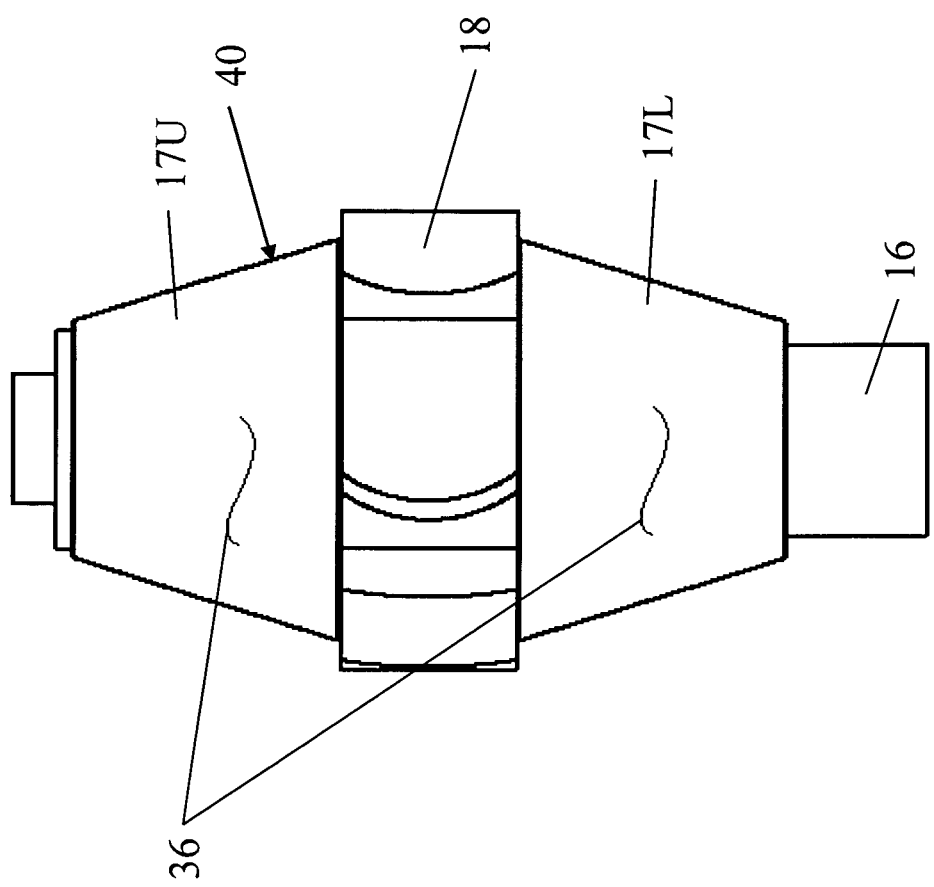
FIG. 4 is a side elevation view of the rotating portion of the bearing assembly.

Referring now to FIG. 4, there is shown an internal rotating component of the cartridge 6 illustrated in FIG. 3, which is a central rotor or rotating bearing assembly 40. Rotor 40 includes a central spindle dental bur holding chuck 16 which may be fixably fitted by a light press fit with two outwardly facing, that is up and down, frusto-conical journals 17U and 17L and a multi bladed impeller turbine 18 or other suitable drive blades.

Preferably, a coating 36 is provided to the outer surface of frusto-conical journals 17 to reduce friction and wear during possible instances of contact during start up and stopping of rotor 40. A preferred coating 36 would be a carbon type coating, preferably diamond like carbon coating (DLC). This diamond like carbon coating (DLC) is applied to the outward facing surfaces of the two frusto-conical journals 17U and 17L.

Figure 5:
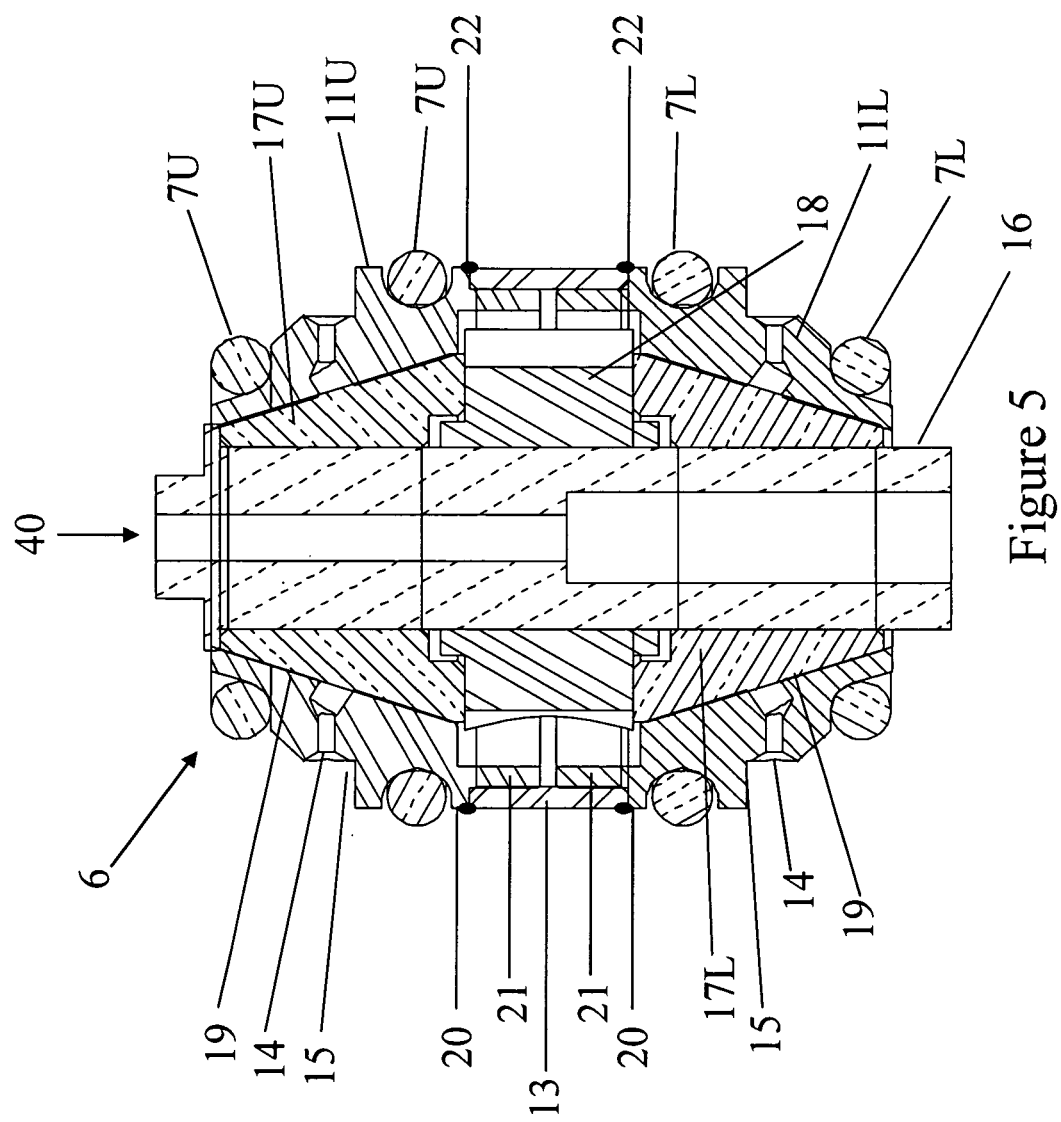
FIG. 5 is a cross sectional view taken along line 5-5 of FIG. 3.

Referring now to FIG. 5, there is shown a cross sectional view of the hydrostatic gas bearing cartridge 6 taken along line 5-5 of FIG. 3 in which there is shown the counter sunk orifice ports 14 which penetrate through the upper and lower cages, 11U and 11L, to gap 19 between the journal 17 and the fixed bearing components formed by the inner surfaces of cages 11U and 11L. The counter sunk orifice ports 14 are connected by circumferential grooves 15. C-shaped spacer 13 is located between the machined cage spacer stops 20. Backing the C-shaped spacer 13 and surrounding the impeller blade tips 18 are the machined backing shoulders 21, which almost touch between the upper and lower cages 11U and 11L. This structure may be secured and sealed by welds 22 permanently fixing upper cage 11U to the C-shaped spacer 13 and the lower cage 11L to the C-shaped spacer 13.

Figure 6:
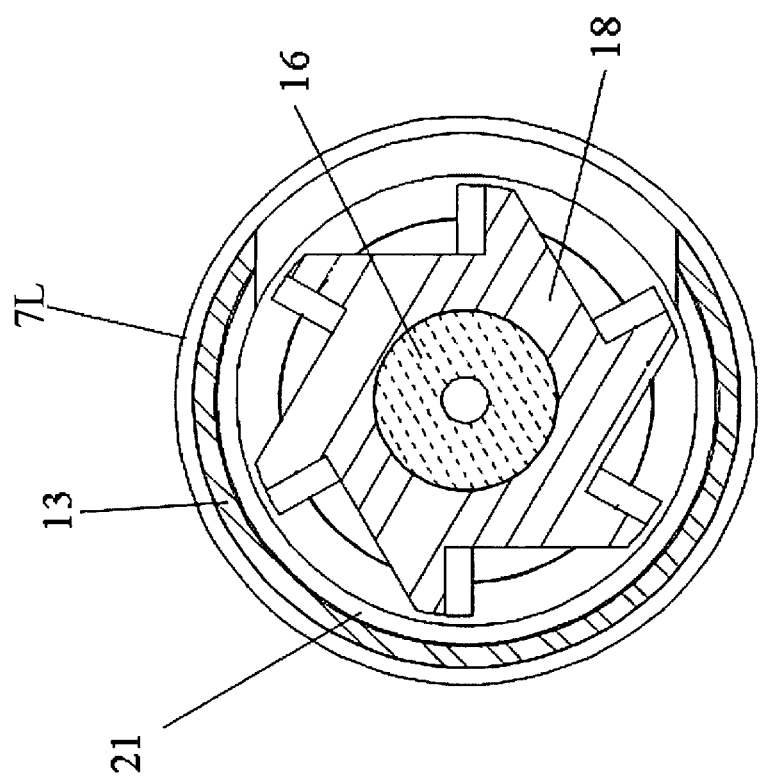
FIG. 6 is a cross sectional view taken along line 6-6 of FIG. 3.

Referring now to FIG. 6 in conjunction with FIG. 5, C-shaped spacer 13 is shown surrounding the impeller 18 by approximately 270 degrees. Backing shoulders 21 are shown to be in close proximity to the tips of the impeller blades 18. Cage spacer stop 20 is shown which engages the edges of C-shaped spacer 13 as best seen in FIG. 5, along with the upper edge of backing shoulder 21.

Figure 7:
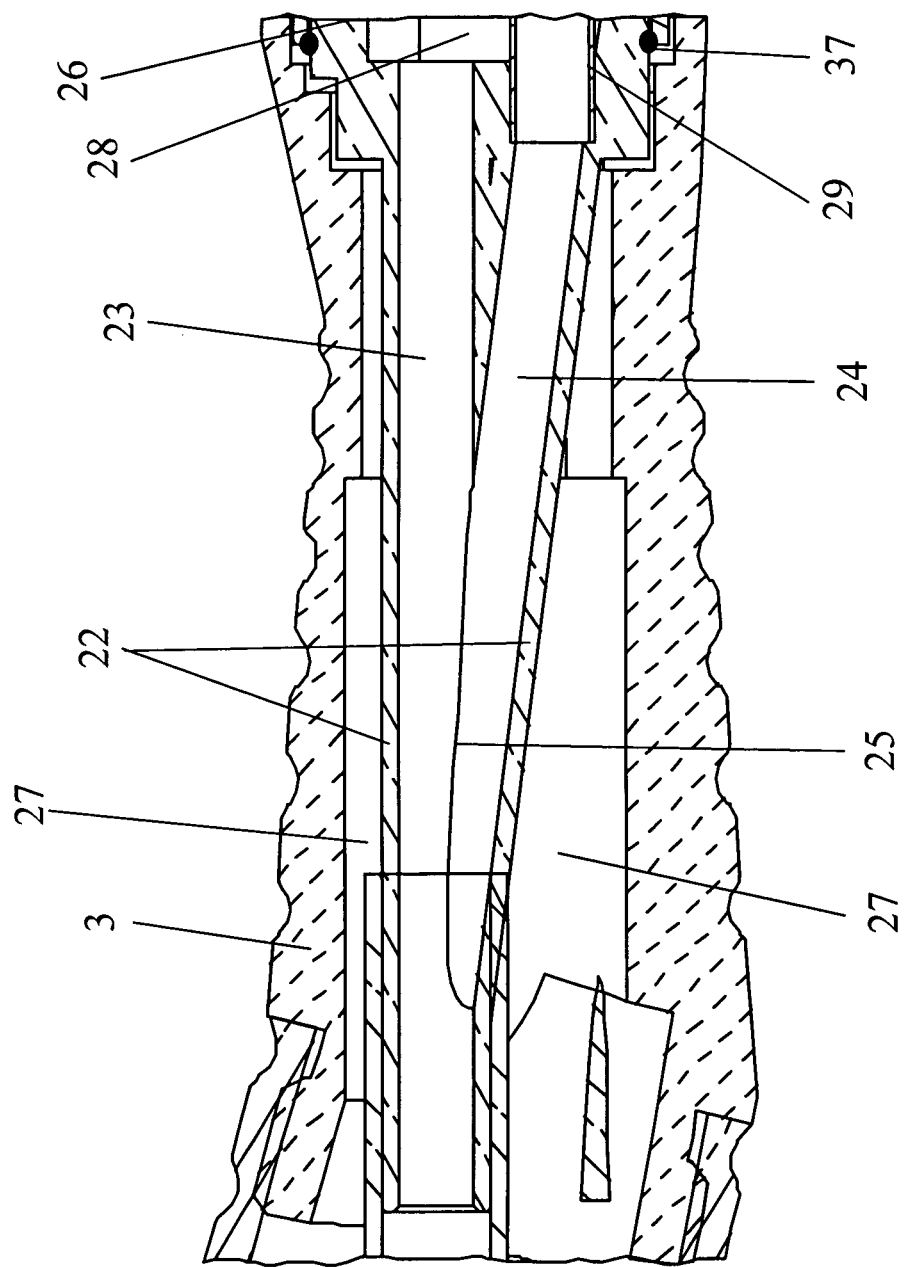
FIG. 7 is a partially broken away cross sectional view taken along line 7-7 of FIG. 2.

Referring now to FIG. 7 there is shown a broken away cross section of grip 3 as taken along the cross section line 7-7 of FIG. 2. FIG. 7 illustrates the tubing input supply for both the turbine drive and the hydrostatic bearings as well as the manifold insert 22 for controlling the air flow between the turbine drive and the hydrostatic bearings as well as the exhaust tubing. Viewing FIG. 7 in conjunction with FIG. 8, there is shown a manifold which may preferably be the form of manifold insert 22 which contains both a substantially straight bearing air supply passageway or tube 23 and a substantially angled turbine air passageway or tube 24. The combination of the straight tube or passageway 23 and the angled passageway 24 form a pneumatic valve 25 which has no moving parts. The pneumatic valve may be formed by various other structures wherein a more direct passageway is provided for fluid flow, such as compressed air, to the space between the rotor and the interior of the cartridge which forms a hydrostatic bearing when supplied with compressed air; as contrasted to the second passageway which is in communication with the turbine blades of the rotor. A more direct passageway may have less turns, curves or restrictions than a less direct passageway which is utilized to supply fluid flow in the form of compressed air to drive the blades of the rotor.

Figure 8:
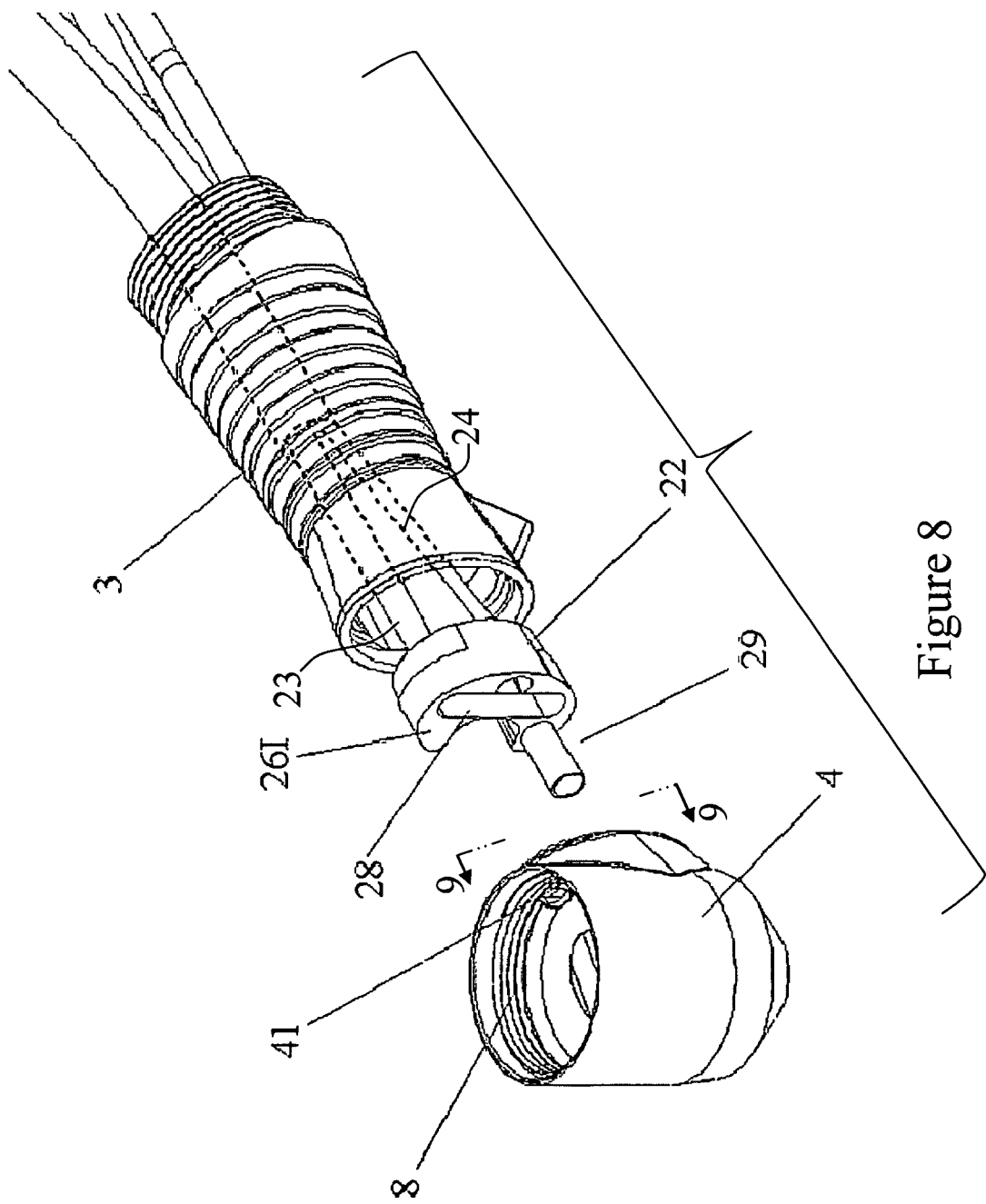
FIG. 8 is a view of perspective of a handpiece in accordance with the present invention including an exploded view of a manifold insert and the connections between the grip and the head portion of the handpiece.
Figure 9:
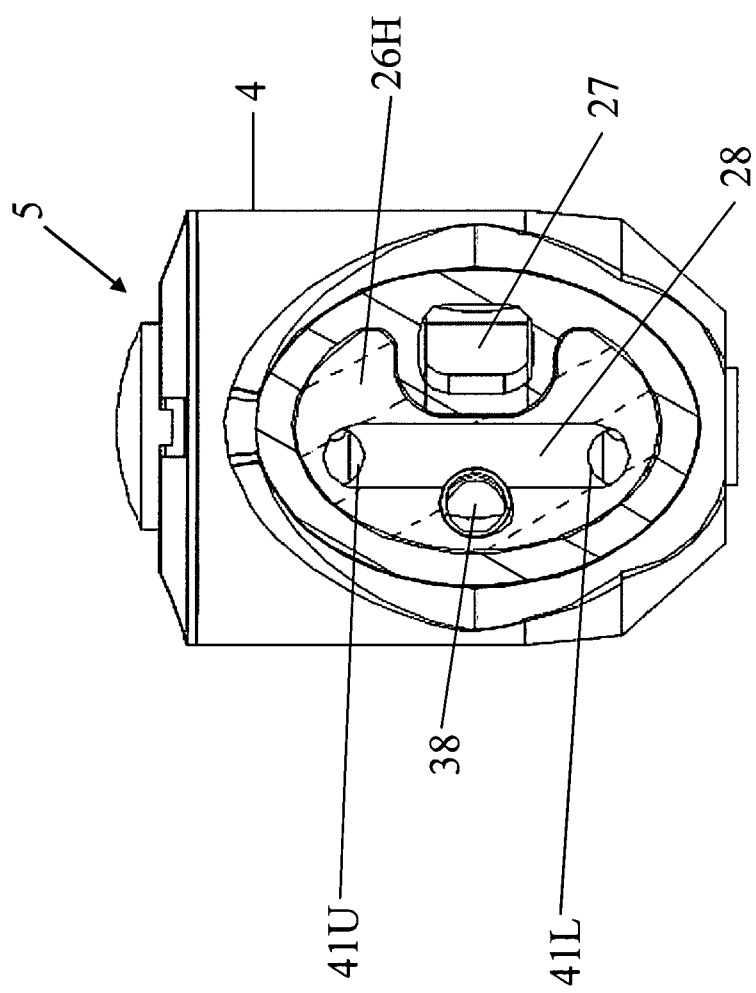
FIG. 9 is an elevation view of head 4 taken in the direction of line 9-9 of FIG. 8.

As may be best seen in FIGS. 7, 8 and 9, face-sealing interface 26 between manifold insert 22 and head 4, are preferably precision machine flat and smooth to form a face sealing interface between the pressurized bearing supply gas such as compressed air and the surrounding exhaust gas passageway 27. The two gas streams are further separated by use of a fixing and sealing weld 37 between manifold insert 22 and head 4. Hydrostatic bearing supply fluid is introduced to both the upper and lower bearing supply chambers via milled slots 28 in both manifold insert 22 and head 4. The combined passageway area of both slots is preferably greater than that of the drive air passageway area. A selectively sizable coupling tube 29 connects the manifold insert 22 to head 4, serving to pass the turbine drive air from the turbine drive air passageway 24 in manifold 22 insert to turbine air orifices 14 in head 4. Because of the limited physical size of grip 3, coupling tube 29 passes the turbine drive air through the location of the bearing gas supply slots 28, while maintaining separate air flow streams.

Continuing to refer now to FIGS. 7, 8 and 9, compressed air or gas supply slot 28 in manifold insert 22 is best seen in FIG. 8. Slot 28 provides compressed air or gas to both upper bearing air supply hole 41U and lower bearing supply air tube 41L as best seen in FIG. 9, which is an elevation view of the interface 26H of head 4. The elevation view of interface 26H of head 4 as shown in FIG. 9 also illustrates the turbine air orifice 38 for compressed air as well as exhaust port 27. The head side of the face sealing interface 26H of FIG. 9 mates with the face sealing interface surface 26I of manifold insert 22, best seen in FIG. 8.

Figure 10:
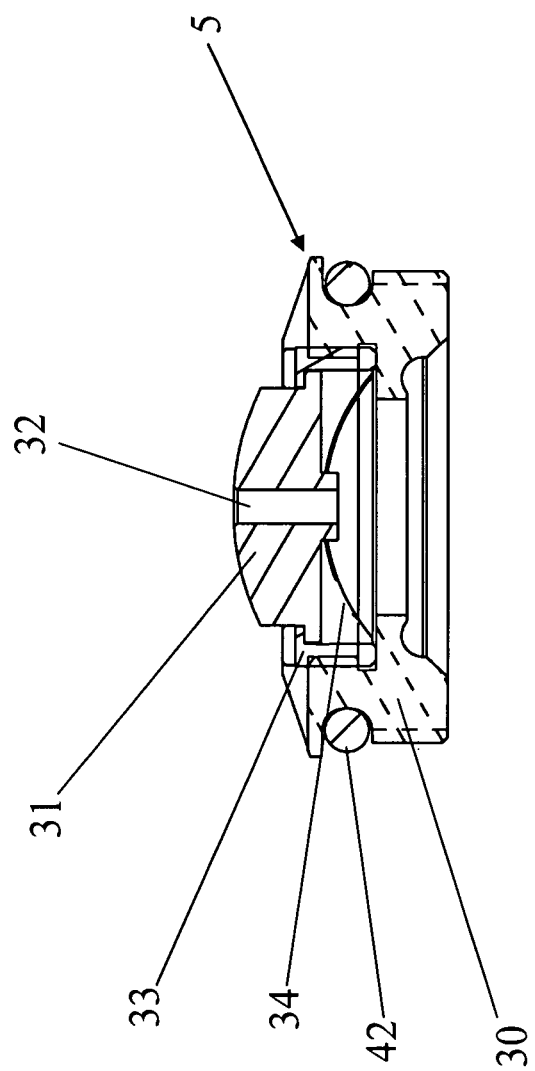
FIG. 10 is a cross sectional view of a cap assembly.

Referring now to FIG. 10, there is shown a cross sectional view of cap assembly 5 which is preferably comprised of a cap 30 and a button 31 that is drilled through to form a balancing vent hole 32. Cap assembly is provided with a retainer 33, spring 34 and sealing O-ring 42.

The present invention includes the use of a C-shaped spacer to provide a level of precision to actively form straight and parallel surfaces on bearing components and to enable assembly of the components into a functional bearing with the required degree of miniscule, uniform and parallel gaps being established between the moving and stationary rotor parts. The present invention uses two interchangeable and identical cages that incorporate a machined shoulder and stop ready to receive a C-shaped spacer. This permits the gap (endplay) of the double ended outwardly facing frusto-conical rotating bearing assemblies to be adjusted readily and quickly. In accordance with the present invention, a C-shaped spacer may be selected at random and a cartridge may be built up using the spacer, measuring the resulting gap and comparing the gap verses the desired gap. Prediction of the best size spacer may be made through a geometric mathematical model based on desired spacing, cone angle, cone length and cage length. Then the final spacer is selected, installed and verified in a gap (endplay) measurement.

Once the spacer selection process is complete the cartridge may be securely fixed together via two welds. A preferred embodiment uses inert gas bath laser welding between the two cages and the C-shaped spacer. The integrally machined stops and shoulders on the cages may be fabricated with care to create a state of parallelism and perpendicularity with respect to the axis of the frusto-conical cavity which eventually receives the rotating bearing assembly. Likewise, a parallelism constraint is placed on the C-shaped spacer during fabrication. Combining the parts creates a self aligning exterior cartridge shell which forms the static (non rotating) portion of the gas hydrostatic bearing. Backing shoulders integrally machined into the cages serve several purposes, firstly, to accurately locate the C-shaped spacer equidistantly from the central axis of the cartridge assembly, secondly, to provide a frame of reference to angularly align the upper and lower cages and the C-shaped spacer so that the cartridge gas inlet/turbine gas exhaust location is formed, and is unobstructed, and thirdly, the height of the shoulders, being slightly less than one half of the height of the smallest design C-shaped spacer yields a confining space for the rotating turbine blade tips that constrains the turbine working fluid within the space of the rotating turbine blades.

Because of the opposing needs of numerous supply tubes within the head of a hydrostatic gas bearing dental handpiece (bearing air, turbine drive air, exhaust, chip and spray water, and fiber optic bundles) and the requirement to have a handpiece with a small head and grip so that the drill head along with the dentist's fingers can be inserted into the mouth, manifold insert 22 was conceived. The design of this insert is such that it reduces the number of tubes in the head thereby reducing required volume. This is achieved by a design of a single bearing gas inlet passageway to supply two bearings by means of various crossways slots 28 in both the manifold insert and the head sealing faces. Due to the alignment of the supply ports of the bearing gas to the upper and lower bearing supply plenums, and the centrally located turbine drive air supply, a coupling tube 29 was designed to bridge the gap through the head and across the bearing air slotting on the sealing face. This coupling tube may be fabricated with a consistent outside diameter and length for locating purposes within the receiving holes in the manifold insert and the head, but may have various internal diameters determined by tubing wall thickness, resulting in various air flow areas for turbine drive air. In selecting this passageway area by test, the resulting balance of airflows between the gas bearings and the turbine drive air may be achieved, in effect restricting or enhancing turbine gas flow while conversely affecting the bearing gas flow. This assures an adequate ratio of gas bearing load capacity versus a particular rotor speed or torque output level.

The manifold insert is designed with a pneumatic valve between the turbine air tube and the bearing air supply tube, in that a stream of air with high velocity passes straightly towards the bearing air distribution slots, but over a tube at an angle toward the turbine air nozzle, thereby drawing slight vacuum on the second tube until overall system backpressure builds. This results in the first or straight tube immediately providing gas flow and gas pressure to the gas bearings before the second or angled tube provides air to the turbine. Such arrangement serves to energize the hydrostatic gas bearings firstly and the turbine secondly, thereby providing non-contact bearing function prior to providing rotor revolution. By having the ability to float the rotor bearing assembly on a film of gas prior to beginning rotation, the likelihood for component wear is greatly reduced.

Moreover, to counteract potential damage in the unlikely event that contact occurs between the rotor bearing assembly and static bearing components, the rotating bearing components (frusto-conical shapes) are coated with a type of carbon coating, such as diamond like carbon coating (DLC) using an RF vapor deposition process to uniformly and conformably coat the cones or frusto-conical shapes with up to a 5 micron thick layer of essentially pure carbon in a diamond like structure. Carbon type coating and DLC coatings provide superior dry lubricity properties. Diamond like carbon provides an excellent dry sliding properties and extremely low coefficient of friction. Another advantage of using the coating process for these frusto-conical shapes is that the process provides a uniform and conformal coat, not likely to impart weight imbalance to the machined cones, which is of critical concern for spindles that rotate at high angular speeds, such as encountered in dental handpieces.

Use of a double-ended rotor with outward facing frusto-conical bearings inherently leads to venting of a portion of the bur-end bearing gas axially along the spindle, exiting the drill between the spindle and the head housing. Operation of a dental drill with such design with a closed head and therefore fully enclosed upper gas bearing leads to an imbalance of bearing load capacities and subsequent inability for the rotor to rotate. The present invention overcomes this by the addition of a bearing gas vent hole in the button, sized appropriately to permit upper bearing exhaust gas to escape to the atmosphere, balanced in amount to that gas escaping to the atmosphere at the bur end.

The present invention may be embodied in other specific forms without departing from the spirit or essential attributes thereof.

We claim:

1. A dental handpiece, comprising:
    a head;
    a grip connected to said head;
    a handle connected to said grip;
    said head containing a removably attached cartridge;
    a rotor mounted in said cartridge, said rotor having two opposing frusto-conical shapes to support the rotor in both the radial and axial directions simultaneously;
    said rotor further comprising a centrally disposed plurality of turbine blades;
    a single fluid inflow tube passing through said handle;
    said inflow tube of said handle being in communication with a bifurcation contained within said grip wherein one passageway is in fluid communication with a plurality of fluid ports on said cartridge for supplying fluid flow to a space between said frusto-conical shapes of said rotor and an interior conforming shape of said cartridge to create a hydrostatic bearing and a second passageway in communication with said turbine blades of said rotor, said first passageway being more direct than said second passageway; and
    exhaust means for fluid flow exiting said head, said exhaust means including means for balancing an upper and lower portion of said fluid flow between said frusto-conical shapes of the bearings of said rotor and the interior of said cartridge.

2. A dental handpiece in accordance with claim 1 wherein said first passageway is more direct than said second passageway as a result of the structure of said first passageway being straight and said second passageway being angled to said first passageway.

3. A dental handpiece in accordance with claim 1 wherein said two opposing frusto-conical shapes of said rotor and mating interior surfaces of said cartridge are coated with a diamond like carbon coating.

4. A dental handpiece in accordance with claim 3 wherein said diamond like carbon coating has a thickness of approximately five microns.

5. A dental handpiece in accordance with claim 1 wherein said bifurcation of said first passageway and said second passageway in said grip are contained in a manifold insert.

6. A dental handpiece, comprising:
    a head;
    a grip connected to said head;
    a handle connected to said grip;
    said head containing a removably attached cartridge;
    a rotor mounted in said cartridge for rotational movement within said cartridge, said rotor having two opposing frusto-conical shapes to support said rotor in both a radial and axial directions simultaneously;
    a plurality of drive blades on said rotor;
    a single inflow tube passing through said handle;
    means for directing fluid inflow from said tube passing through said handle first to a space between said rotor and said cartridge forming an air bearing and thereafter to said blades of said rotor causing said rotor to rotate after air has been supplied to said air bearings; and exhaust means for fluid flow exiting said head, said exhaust means including means for exhausting fluid flow from an upper portion of said head.

7. A dental handpiece in accordance with claim 6 wherein said means for directing fluid inflow comprises a manifold insert having a more direct fluid flow passageway to said space between said rotor and said cartridge and a less direct fluid passageway to said blades of said rotor.

8. A dental handpiece in accordance with claim 7 wherein said more direct passageway is a straight tube and wherein said less direct passageway is a tube angled to said straight tube, said straight tube and said angled tube being in communication with each other and said communication occuring within a manifold insert mounted within said grip.

9. A dental handpiece in accordance with claim 6 wherein said blades of said rotor are turbine blades.

10. A dental handpiece, comprising:
a head;
a grip connected to said head;
a handle connected to said grip;
said head containing a removably attached cartridge;
a rotor mounted in said cartridge for rotational movement, said rotor having two opposing frusto-conical shapes to support said rotor in both a radial and an axial direction simultaneously;
said rotor having a plurality of drive blades;
a fluid inflow passageway manifold which provides fluid flow to a space between said rotor and said cartridge prior to applying fluid flow to said drive blades to cause rotation of said rotor;
said cartridge containing an upper and lower frusto-conical shaped cage and a C-shaped spacer mounted between said cages; and
exhaust means for the fluid flow existing said head.

11. A dental handpiece in accordance with claim 10 wherein said frusto-conical shapes of said rotor and mating interior surfaces of said cages are provided with a diamond like carbon coating.

12. A dental handpiece in accordance with claim 10 wherein said air passageways are in the form of a manifold which is inserted into said grip portion.

13. A dental handpiece in accordance with claim 12 wherein said manifold includes a substantially straight line airflow to said space between said rotor and said cages comprising a hydrostatic air bearing and an angled passageway providing fluid flow to drive said drive blades of said rotor.

14. A dental handpiece in accordance with claim 13 including a coupling tube of selectable size mounted on an outflow side of said manifold to balance fluid flow supplied to said space forming said hydrostatic bearing and that supplied to said drive blades.

15. A dental handpiece in accordance with claim 10 wherein said drive blades are turbine blades.

\* \* \* \* \*